United States Patent [19]

Jansen et al.

[11] Patent Number: 4,670,563

[45] Date of Patent: Jun. 2, 1987

[54] IMIDAZOLIDES AS INTERMEDIATES FOR THE SYNTHESIS OF CYTOTOXIC CONJUGATES

[75] Inventors: Franz Jansen, Castries; Pierre Gros, Montpellier, both of France

[73] Assignee: Sanofi, Paris, France

[21] Appl. No.: 743,659

[22] Filed: Jun. 11, 1985

[30] Foreign Application Priority Data

Jun. 20, 1984 [FR] France .................................. 84 09704
Jun. 20, 1984 [FR] France .................................. 84 09703

[51] Int. Cl.[4] ............................................. C07D 401/06
[52] U.S. Cl. .................................... 546/278; 548/341; 548/336
[58] Field of Search ................. 548/336, 341; 546/278

[56] References Cited

U.S. PATENT DOCUMENTS 4,340,535 7/1982 Voisin et al. ........................... 424/85
4,450,154 5/1984 Masuho et al. ............... 260/112.5 R

FOREIGN PATENT DOCUMENTS 23401 2/1981 European Pat. Off. .
44167 1/1982 European Pat. Off. .
80401 8/1983 European Pat. Off. .
82/8048 of 0000 South Africa .

OTHER PUBLICATIONS

Fukuoka et al. CA 90:164345a

*Primary Examiner*—Jane T. Fan
*Attorney, Agent, or Firm*—Bacon & Thomas

[57] ABSTRACT

Imidazolides of the formula:

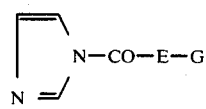

in which:
E represents an inert spacing structure; and
G represents a group:

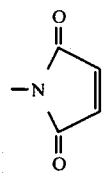

or a group —S—S—X, in which X is an activating group.

Application: synthesis of cytotoxic conjugates.

2 Claims, No Drawings

IMIDAZOLIDES AS INTERMEDIATES FOR THE SYNTHESIS OF CYTOTOXIC CONJUGATES

The present invention relates to new imidazolides and a process for their preparation. The imidazolides according to the invention are especially suitable as agents for coupling proteins, in particular for the synthesis of cytotoxic conjugates which can be used in therapy.

The compounds according to the invention correspond to the formula:

$$\text{N} \diagdown \text{N—CO—E—G} \qquad \text{I}$$

in which:
E is an inert spacing structure; and
G represents a group:

(maleimide group with two C=O and N)

or a group —S—S—X, in which X is an activating group.

The term "inert spacing structure", as used in the present description, denotes a divalent organic radical which is inert towards the reactants used in the process for the synthesis of cytotoxic conjugates, such as a straight-chain or branched alkylene group containing from 1 to 15 carbon atoms, which can contain one or more double bonds, can be interrupted by oxygen atoms or can be substituted by one or more inert functional groups such as methoxy groups, free or esterified carboxyl groups, dialkylamino groups or carbamate groups. The same term also denotes an arylene group containing from 6 to 15 carbon atoms, which can be substituted by one or more inert functional groups as indicated above for the alkylene group.

The term "activating radical", as used here for X, denotes a group bonded to an —S—S— bridge capable of reacting with a free thiol to form a disulfide with the release of X—SH. Suitable activating radicals are pyridin-2-yl and pyridin-4-yl groups which are unsubstituted or substituted by one or more halogens or alkyl, carboxyl or alkoxycarbonyl radicals; the phenyl group which is unsubstituted or, preferably, substituted by one or more halogens or nitro, alkoxy, carboxyl or alkoxycarbonyl groups; or an alkoxycarbonyl group such as methoxycarbonyl.

The terms "alkyl" and "alkoxy" denote groups containing up to 5 carbon atoms.

The term "alkylene" denotes straight-chain or branched, saturated aliphatic groups containing up to 10 carbon atoms, which can be substituted by one or more inert functional groups such as alkoxycarbonyl groups.

The compounds of the formula I in which E represents an alkylene group as defined above are particularly suitable as agents for coupling proteins.

The compounds of the formula I in which E represents a group —(CH$_2$)$_p$—, in which p is between 2 and 7, or a group of the formula $$-\text{CH}-\text{CH}_2\text{COOH}$$

are preferred.

Particular preference is given to the compounds of the formula I in which E represents a group —(CH$_2$)$_p$—, in which p is an integer from 2 to 7, or a group:

$$-\text{CH}-$$
$$\ \ |$$
$$\text{CH}_2\text{COOH}$$

and G is a group of the structure —S—S—X, in which X is an activating radical chosen from pyridin-2-yl and pyridin-4-yl groups which are unsubstituted or substituted by one or more halogens or alkyl, carboxyl or alkoxycarbonyl radicals; the phenyl group which is unsubstituted or substituted by one or more halogens or nitro, alkoxy, carboxyl or alkoxycarbonyl groups; or an alkoxycarbonyl group.

The new compounds of the formula I are prepared by a process which consists in reacting a compound of the formula:

$$\text{G—E—COOH} \qquad \text{II}$$

in which G and E are as defined above, with carbonyldiimidazole of the formula:

$$\text{N} \diagdown \text{N—CO—N} \diagup \text{N} \qquad \text{III}$$

in an organic solvent, at a temperature of 10° to 40° C. Ether solvents, such as dioxane and tetrahydrofuran, are particularly preferred.

The compounds of the formula I are particularly useful as agents for coupling with the hydroxyls of the tyrosines of proteins, such as the proteins A and P defined below, to give the conjugates or immunotoxins which form the subject of the French patent application No. 84 09703 in the name of the Applicant Company and entitled "New cytotoxic conjugates which can be used in therapy and process for their preparation and priority of which is claimed in co-pending U.S. application Ser. No. 743,615 also filed June 11, 1985."

These immunotoxins correspond to the following statistical formula:

$$\text{P}'\text{—W—A}' \qquad \text{IV}$$

in which P' represents the radical of a protein P which is an antibody or a fragment of an antibody, as such or appropriately chemically modified, from which one or more of its own groups have been removed and in which the other functional groups are optionally blocked, A' represents the radical of a protein which is the subunit A of ricin, as such or appropriately chemically modified, from which at least one of its own groups has been removed and in which the other functional groups are optionally blocked, and W represents a divalent covalent structure containing a thioether group or a disulfide group in which either the sulfur atoms are those of the cysteines of P and A or they are bonded to the groups belonging to P and/or A by spacing structures carrying a functional group bonded to the said groups belonging to P and/or A, with the limitation that, in the case where W contains a disulfide group, when one of the sulfur atoms of the said disulfide is that belonging to one of the cysteines of A, the other sulfur is bonded to the protein P by a spacing structure carrying a functional group bonded to a group of the protein P other than an amine group.

A thioether bond between two proteins is understood as meaning a bond of the type:

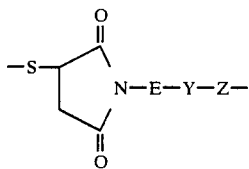

in which Z, Y and E are as defined below.

The preferred immunotoxins correspond to the statistical formula:

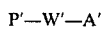         V in which P' and A' are as defined above and W' represents a covalent structure chosen from:

(a) a group of the formula:

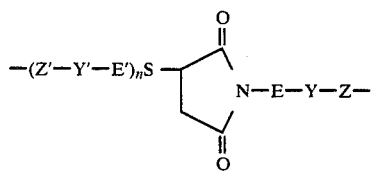

(b) a group of the formula:

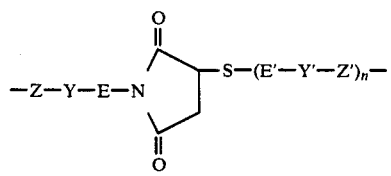

(c) a group of the formula:

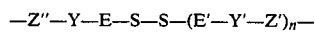

or (d) a group of the formula:

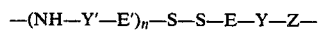

in which:

Z and Z' represent the groups belonging to the proteins A and P, chosen from the oxygen atom originating from the hydroxyl of one of the tyrosine residues, the carbonyl group originating from one of the terminal carboxyls or the free carboxyls of the aspartic and/or glutamic acids of A and P, the group originating from the dialdehyde structure obtained after oxidation of the carbohydrate structure of P with periodic acid, and the —NH— group originating from one of the terminal amines of A and P or from one of the amines in the epsilon position of one of the lysine residues;

Z" is as defined above for Z and Z' but cannot be —NH—;

Y and Y' represent functional groups capable of bonding covalently with any one of the groups Z, Z' and Z" of the proteins A and P;

E and E' represent inert spacing structures; and n represents zero or 1.

The immunotoxins above are represented in simplified form by the formulae IV and V, but it is understood that the divalent covalent structure —W— or —W'— is bonded to at least one molecule P and at least one molecule A. The number of bonds with the proteins P and A depends on the number of groups belonging to the said proteins which are involved in the coupling operation.

For example, if an immunotoxin is formed by the coupling of the sub-unit A of native ricin with the antibody P (for example the antibody T101) via a divalent covalent structure having a disulfide group in which one sulfur is that belonging to the 257-cysteine of the A chain of ricin and the other is bonded to the phenolic oxygens of the tyrosines of the antibody P by an oxopropyl group, it will have the statistical formula:

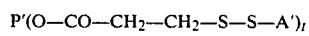

in which t represents the number of tyrosines in the antibody (for example the antibody T101) which are involved in the coupling.

The resulting immunotoxin thus corresponds to a product of the formula V in which:

P' is as defined above, especially the radical of the antibody T101 from which t phenolic groups of its tyrosines have been removed;

A' is as defined above, especially the radical of the A chain of ricin from which the thiol group of its 257-cysteine has been removed; and W' is the group (c):

in which Z" is the oxygen of the phenolic hydroxyls involved in the coupling, Y is —CO—, E is the inert spacing structure —CH$_2$—CH$_2$— and n is zero.

Particular preference is given to the immunotoxins formed by one or more structures containing the sub-unit A of ricin and a single antibody P, which are represented by the statistical formula:

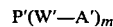         VI in which P', W' and A' are as defined above and m represents the number of groups belonging to the protein P which are involved in the coupling. The number m varies from 0.3 to 12, preferably from 0.5 to 10.

The expression "m varies from 0.3 to 12, preferably from 0.5 to 10" means that the value of m is a statistical value because the coupling does not take place homogeneously within the population of antibody molecules. The number m may therefore not be an integer.

The value of m depends especially on the antibodies used and more particularly on their molecular weight.

Thus, if a fragment Fab or Fab' is used as the starting antibody P, the value of m can vary between 0.3 and about 2; if a fragment F(ab')$_2$ is used, m can vary between 0.5 and about 4; for an antibody of the IgG type, the value of m will be between 0.5 and 6; finally, for an antibody IgM, the value of m can vary between 1 and 12.

It is preferable, however, for the degree of substitution on the antibody P to be such as to lead to a value of m which is not less than 0.5 and not more than 10.

More generally, the structures IV and V above represent statistical formulae written in simplified form, as already explained.

Analogously, the formulae VII, VIII and IX below are also statistical formulae—whenever n is 1—because the coupling reactants are prepared from populations of proteins $P_1$ and $P_2$ which all have exactly the same properties as those taken into account above for the antibody P, whether these proteins $P_1$ and $P_2$ themselves are the antibody P or the A chain of ricin.

The immunotoxins having the above structure IV may be obtained by the process wherein a protein $P_1$, which is arbitrarily either the optionally modified sub-unit A of ricin or an antibody or a fragment of an antibody, carrying at least one free thiol group attached to the said protein $P_1$ directly or via a spacing structure, is reacted, in aqueous solution and at ambient temperature, with a protein $P_2$ different from $P_1$, which is arbitrarily either the sub-unit A of ricin or an antibody or a fragment of an antibody, carrying a group capable of coupling with the free thiol of the protein $P_1$ to form a thioether or disulfide bond, with the limitation that, in the case of the formation of the disulfide bond, when the protein $P_1$ is the sub-unit A of ricin, the bond with the protein $P_2$ is formed with a group of the said protein $P_2$ other than the amine groups.

According to a preferred feature, the process for the preparation of an immunotoxin having structure V, in which P', W' and A' are as defined above, consists in reacting, in an aqueous solution and at room temperature, a protein of the formula:

$$P_1'-(Z-Y-E)_n-SH \qquad \text{VII}$$

with a protein of the statistical formula:

$$P_2'-Z'-Y'-E'-G \qquad \text{VIII}$$

in which $P_1'$ and $P_2'$ represent the radicals of the proteins $P_1$ and $P_2$ bonded to the groups belonging to the said proteins, or the radicals of one of the protein $P_1$ or $P_2$ originating from the opening of the carbohydrate structures of antibodies or antibody fragments by reaction with periodic acid, Z, Z', Y, Y', E and E' are as defined above and G represents a group:

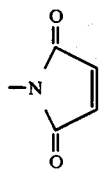

or a group —S—S—X, in which X is an activating group, is being understood that, when G is a group —S—S—X and $P_1'$ is the sub-unit A of ricin, n is 1 or alternatively n can be zero, but, in this case, Z' is other than —NH—.

Therefore, both P and A are proteins which arbitrarily have:

(1) the thiol group or groups taking part in the coupling, and (2) one or more functional groups capable of reacting with the above thiol groups to form a disulfide or thioether bond.

In the present specification, the said thiol groups and functional groups are those of the native proteins P or A or alternatively are introduced therein artificially.

For reasons of clarity, there now follows a description of the meaning of the symbols used to denote the above proteins or their radicals and of the expressions used to denote the various symbols.

The symbol P represents a protein chosen from any antibody or fragment of an antibody, any immunoglobulin or fragment of an immunoglobulin, or any molecule derived from these molecules by artifical modification of any one of their functional groups, including carbohydrate structures which they carry, with the proviso that the chosen protein is still capable of selectively recognizing a given antigen on the surface of the cells carrying this antigen, especially cancerous cells.

The symbol A represents a protein which is the sub-unit, called the A chain, of the plant toxin ricin, such as can be obtained directly from natural ricin, or any molecule derived from this A chain by artificial modification of any functional group carried by this protein with the proviso that the chosen protein still has the property of inhibiting ribosomal protein synthesis in the eucaryotic cells, as can be demonstrated in an acellular study model.

The symbol P' represents a radical derived from the above protein P, as such or appropriately chemically modified, from which one or more of its own groups have been removed and in which other functional groups are optionally blocked.

The symbol A' represents a radical derived from the above protein A, as such or appropriately chemically modified, from which one or more of its own groups have been removed and in which other functional groups are optionally blocked.

The symbol $P_1$ represents one of the proteins A and P as defined above, which carries free thiol groups attached to the said protein directly or via a spacing structure.

The symbol $P_2$, which is different from $P_1$, represents one of the proteins A and P as defined above, which carries one or more functional groups capable of reacting with the free thiols.

The symbol $P_1'$ represents that radical of the protein $P_1$ which is bonded to the groups belonging to the protein $P_1$, especially the groups SH (of the cysteine), $NH_2$ (in the terminal position of the protein or in the epsilon position of the lysines), OH (of the tyrosines) or COOH (of the aspartic and glutamic acids), or that radical of the protein $P_1$ which originates from the opening, by reaction with periodic acid, of the carbohydrate structures, when $P_1$ is an antibody or an antibody fragment.

The symbol $P_2'$ represents that radical of the protein $P_2$ which is bonded to the characteristic functional groups $NH_2$ (in the terminal position of the protein or in the epsilon position of the lysines), OH (of the tyrosines) or COOH (of the aspartic and glutamic acids).

For example, $P_1'$—SH represents the protein $P_1$ (which can arbitrarily be the antibody or antibody fragment P or the sub-unit A of ricin) in which the SH groups of the cysteines are free and the other functional groups are optionally blocked.

In the same way, $P_1'$—CO— represents the protein $P_1$ in which the terminal carboxyl group or the carboxyl groups of its glutamic and aspartic acids are coupled with a group which artificially introduces an SH group.

Again, $P_2'$—NH— represents the protein $P_2$ (which can arbitrarily be the antibody or antibody fragment P or the sub-unit A of ricin) in which the terminal amino group or the amino groups of its lysines are attached to a group capable of coupling with the thiol of the protein $P_1$.

The expression "functional group capable of bonding covalently", as used here for Y and Y', denotes any groups capable of reacting with the groups belonging to the proteins $P_1$ and $P_2$ to give a covalent bond. Thus, the groups —CO— and —(C=NH)— are suitable functional groups capable of bonding with the free amines, the thiols and the phenolic hydroxyls of the proteins. Likewise, the —NH— group is a suitable functional group capable of bonding with the free carboxyl groups of the proteins. The group =N— is a suitable functional group capable of bonding with the two carbon atoms of the carbohydrate structures of the proteins $P_1$ or $P_2$ after oxidation with periodate ions, when $P_1$ or $P_2$ is an antibody or antibody fragment.

The expression "group belonging to the proteins", as used here for Z, Z' and Z'', denotes the radicals originating from the characteristic groups of the amino acids forming the proteins $P_1$ and $P_2$, such as the oxygen atom originating from the hydroxyls of the tyrosine and possibly serine amino acids, the carbonyl group originating from the terminal carboxyl or the free carboxyls of the aspartic and glutamic acids, the —NH— group originating from the terminal amine of the proteins or the lysines, or the sulfur atom originating from the thiol of the cysteine. The same expression also denotes the group originating from the dialdehyde structure obtained after oxidation of one of the carbohydrate structures of the proteins $P_1$ or $P_2$ by treatment with periodate ions, when $P_1$ or $P_2$ is antibody or antibody fragment.

The preparation of the pure A chain of ricin, which is necessary for obtaining the products of the present invention, has been described in U.S. Pat. No. 4,340,535. The preparation of monoclonal antibodies directed against human cancerous cells has been widely mentioned in the scientific literature and many of these antibodies are now commercially available.

The chemical coupling of the A chain of ricin with the antibody (or antibody fragment) can be effected according to the procedures which:
preserve the respective biological activities of the two components of the conjugate, namely the antibody and the A chain of ricin,
ensure that the process has a satisfactory reproducibility and a good coupling yield,
make it possible to control the value of the ratio A chain of ricin/antibody in the conjugate obtained,
lead to a stable and water-soluble product.

Among the procedures corresponding to these characteristics, preference must be given to those which involve one or more thiol groups for forming the bond between the 2 proteins. In fact, these thiol groups are particularly suitable for forming either disulfide bonds or thioether bonds, both of which satisfy the general conditions above.

In general, in order to carry out the coupling reactions between proteins successfully and to eliminate disordered crosslinkings in particular, it is important for one of the proteins to be coupled, and one only, to carry the thiol or thiol groups to be used, while the other protein only carries one or more groups capable of reacting with the thiols in an aqueous medium having a pH of between 5 and 9, and at a temperature not exceeding 30° C., to produce a stable and clearly defined covalent bond.

The characteristics of the proteins $P_1$ and $P_2$ used as starting materials are illustrated in detail below. The spacing structures E can be replaced by the preferred structures R to $R_8$, which are only given as examples.

I—THE PROTEIN $P_1$

As this protein is in all cases the one carrying the thiol group or groups which take part in the coupling, the situation which arises varies according to the nature of this protein $P_1$.

(A) The protein $P_1$ carries, in the natural state, one or more thiol radicals which can be used to permit coupling with the protein $P_2$; this is particularly the case if the protein $P_1$ is the antibody fragment known as F(ab)', as conventionally obtained by the limited proteolysis of the antibody in the presence of pepsin, followed by reduction of the disulfide bridge (or bridges) between high-molecular chains.

This is also the case if the protein $P_1$ is the A chain of ricin or a derivative of this A chain in which at least one of the thiol groups carried by the 171-cysteine and 257-cysteine residues of the A chain of native ricin is free and accessible for chemical coupling.

In all these cases, the protein $P_1$ carrying its natural thiol group (or groups) can be used in this state for the coupling step.

(B) The protein $P_1$ does not carry, in the natural state, thiol radicals which can be used to permit coupling with the protein $P_2$:
this is especially the case if the protein $P_1$ is a native immunoglobulin, a whole antibody or a fragment of an antibody, especially one of the fragments commonly called F(ab)'$_2$ or F(ab);
another case in which the protein $P_1$ does not carry, in the natural state, a thiol group which can be used for coupling is the case where this protein $P_1$ is the A chain of ricin in which each of the two cysteine residues is either blocked by alkylation or inaccessible for chemical modification.

In all cases, it will thus be appropriate artificially to introduce into such molecules one or more thiol groups capable of permitting coupling.

Three types of reaction can preferably be used for the introduction of thiol groups:

1—The first type of reaction is with S-acetylmercaptosuccinic anhydride, which is capable of acylating amine groups of the protein. It will then be possible to free the thiol groups by reaction with hydroxylamine to remove the acetyl protecting radical, in the manner already described (Archives of Biochemistry and Biophysics, 119, 41–49, 1967). It will even be possible, in the case where the thiol group (or groups) thus introduced in the protected form are subsequently to react with an activated mixed disulfide radical, to dispense with the prior deprotection by means of hydroxylamine; in fact, the reaction for forming the disulfide bond using the reactants forming the subject of the present invention takes place just as well with the S-acetyl radical as with the free thiol.

Other methods described in the scientific literature can also be used to introduce thiol groups into the protein to be modified.

2—The second type of reaction consists in reacting the protein via its carboxyl groups with a symmetrical diamino molecule having a disulfide bridge, of the formula:

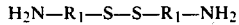

$$H_2N-R_1-S-S-R_1-NH_2$$

in which $R_1$ is an aliphatic group containing from 2 to 5 carbon atoms.

The reaction is preferably carried out with cystamine $[R_1=-(CH_2)_2-]$ in the presence of a coupling agent such as carbodiimide and especially a water-soluble derivative like 1-ethyl-3-dimethylaminopropyl3-carbodiimide, and leads to the formation, depending on the stoichiometries used, one of the following derivatives or a mixture of both:

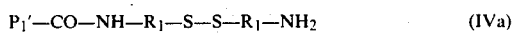

$$P_1'-CO-NH-R_1-S-S-R_1-NH_2 \quad (IVa)$$

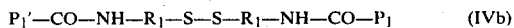

$$P_1'-CO-NH-R_1-S-S-R_1-NH-CO-P_1 \quad (IVb)$$

A reaction product of this type can then be used in two ways:

(a) If, in the formulae IVa or IVb, the protein $P_1$ is the A chain of ricin or one of its derivatives, the reaction medium obtained is subjected, without fractionation, to the action of a reducing agent such as 2-mercaptoethanol, which gives a single protein derivative of the general formula:

$$P_1'-CONH-R_1-SH.$$

The product thus obtained is then purified by dialysis or gel filtration.

(b) If, in the formulae IVa and IVb, the radical $P_1'$ is that radical of the protein $P_1$ which consists of an antibody or one of its fragments, the reaction medium obtained will be used as such for the coupling, in which case a thiol/disulfide exchange method will be used, for example the one described by Gilliland and Collier (Cancer Research, 40, 3564, 1980).

3—The third type of reaction consists in using carbohydrate units, which are present in the natural state in the antibodies, in order to fix the radical carrying the thiol which it is proposed to introduce. The protein is then subjected to oxidation with periodate ions in order to create aldehyde groups on the carbohydrate units. After the reaction has been stopped by the addition of excess ethylene glycol and the by-products and excess reactants have been removed by dialysis, the product obtained is treated with a symmetrical diamino molecule having a disulfide bridge, of the general formula:

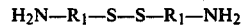

$$H_2N-R_1-S-S-R_1-NH_2$$

in which $R_1$ is an aliphatic group containing from 2 to 5 carbon atoms. The addition products formed are then reduced to secondary or tertiary amines by reaction with a suitable metal hydride, especially sodium borohydride. The reaction is preferably carried out with cystamine $[R_1=-(CH_2)_2-]$ and leads to the formation, depending on the stoichiometries used, of one of the following derivatives or a mixture of both:

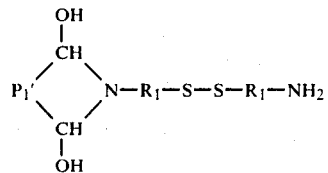

Va

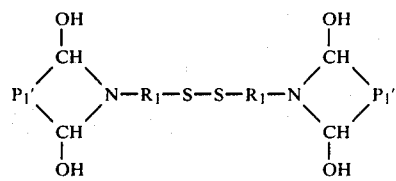

Vb

The reaction medium obtained may then be treated exactly as indicated above for the products characterized by the structures IVa or IVb, wherein $P_1'$ is an antibody or an antibody fragment.

In the last two types of reaction, described above, for the artificial introduction of thiol groups (the types using a symmetrical diamino disulfide reactant), the protein $P_1$ used preferably possesses neither free SH groups nor free amino groups.

In the case of the A chain and its derivatives, this can always be achieved by alkylation of the natural SH group or groups by reaction with a customary reagent for thiols, such as N-ethylmaleimide or iodoacetic acid or one of its derivatives, and by methylation of the natural $NH_2$ groups in accordance with the reductive methylation process described by MEANS and FEENEY (Biochemistry 7, 2192 (1968)). Up to 6 methyl radicals per mol can thus be introduced into the A chain of native ricin. The protein modified in this way retains all of its biological properties and especially its capacity to inhibit ribosomal protein synthesis in the eucaryotic cells.

In the cases of antibodies or antibody fragments and, more generally, all the substances of the first group, as defined previously, which do not possess naturally free SH groups, it will be appropriate to carry out a reductive methylation, for example by the method of MEANS and FEENEY; in this way, it is usually possible to introduce several dozen methyl radicals per mol of antibody without modifying its capacity to selectively recognize an antigen on the surface of the cells carrying this antigen.

II—THE PROTEIN $P_2$

This protein is in all cases the one which carries one or more functional groups capable of reacting with the thiols of the protein $P_1$ to form either a disulfide or a thioether bond. These functional groups, which are always introduced artificially into the protein $P_2$, differ according to whether it is desired to effect coupling by a disulfide bond or by a thioether bond and are chosen as indicated below.

(1) The disulfide bond

In this case, the preparation of the conjugate can be represented by the equation:

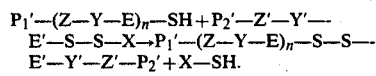

$$P_1'-(Z-Y-E)_n-SH + P_2'-Z'-Y'-E'-S-S-X \rightarrow P_1'-(Z-Y-E)_n-S-S-E'-Y'-Z'-P_2' + X-SH.$$

The protein $P_2$ substituted by an activated sulfur atom is obtained from the protein $P_2$ itself or from the correctly protected protein $P_2$ by substitution with the aid of a reagent which itself carries an activated sulfur atom, according to the equation:

$$P_2 + L-Y'-R-S-S-X \rightarrow P_2'-Z'-Y'-R-S-S-X$$

in which:

$P_2$ denotes the protein to be substituted and

L—Y' represents a group permitting the covalent fixation of the reagent to the protein.

The functional group L—Y' is a group capable of bonding covalently with any one of the groups carried by the side chains of the constituent amino acids of the protein to be substituted. Among these groups, the following will be singled out in particular:

the phenol groups of the tyrosyl radicals contained in the protein. In this case, L—Y' can represent especially an imidazol-1-ylcarbonyl group, which reacts with the phenol groups of the protein according to the equation:

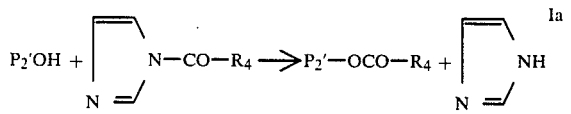

in which the imidazol-1-yl is L, the CO group is Y' and $R_4$ is the group —R—S—S—X. The compound of formula Ia is an imidazolide according to the invention.

The radical —S—S—X denotes an activated mixed disulfide capable of reacting with a free thiol radical. In particular, in this mixed disulfide, X can denote a pyridin-2-yl or pyridin-4-yl group optionally substituted by one or more alkyl, halogen or carboxy radicals. X can also denote a phenyl group preferably substituted by one or more nitro or carboxyl groups. Alternatively, X can represent an alkoxycarbonyl group such as the methoxycarbonyl group.

The radical R denotes the spacing structure (indicated as E in the general formula II above) capable of carrying the substituents Y' and S—S—X simultaneously. It must be chosen so as not to contain groups capable of interfering, during the subsequent reactions, with the reactants used and the products synthesized. In particular, the group R can be a group —(CH$_2$)$_n$—, n being between 1 and 10, or alternatively a group:

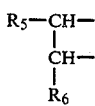

in which $R_6$ denotes hydrogen or an alkyl group having from 1 to 8 carbon atoms and $R_5$ denotes a substituent which is inert towards the reactants to be used subsequently, such as a carbamate group:

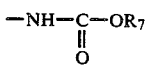

in which $R_7$ denotes a linear or branched alkyl group having from 1 to 5 carbon atoms, especially the tert.-butyl group. The reaction of the compound L—Y'—R—S—S—X with the protein $P_2$ is carried out in a homogenous liquid phase, most commonly in water or a buffer solution. If necessitated by the solubility of the reactants, a water-miscible organic solvent can be added to the reaction medium at a final concentration which can reach 20% by volume in the case of tertiary alcohol, such as tertiary butanol, or 10% by volume in the case of dimethylformamide or tetrahydrofuran.

The reaction is carried out at ambient temperature for a time varying from a few minutes to a few hours, after which the low molecular weight products, and in particular the excess reactants, can be removed by dialysis or gel filtration. This process usually makes it possible to introduce between 1 and 15 substituent groups per mol of protein.

When using such compounds, the coupling with the protein $P_1$ is carried out by bringing the two proteins together in an aqueous solution having a pH of between 6 and 8, at a temperature not exceeding 30° C., for a time varying from 1 hour to 24 hours. The aqueous solution obtained is dialyzed, if appropriate, to remove the low molecular weight products, and the conjugate can then be purified by a variety of known methods.

(2) The thioether bond

In this case, the preparation of the conjugate consists in reacting $P_1'$—(Z—Y—E)$_n$—SH with the protein $P_2$ into which one or more maleimide radicals have been introduced beforehand.

The reaction is then represented by the following equation, which is given as an example:

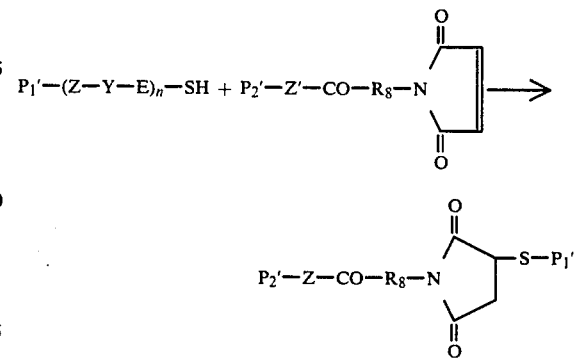

in which:

$R_8$ represents an aliphatic or aromatic spacing structure containing from 1 to 15 carbon atoms, which is inert towards the reactants to be used subsequently, and Z represents groups which can vary according to the type of functional group of the protein $P_2$ involved in the coupling. Thus, Z=oxygen in the case of an ester on the phenol of a tyrosyl residue; Z=NH in the case of the coupling of an activated carboxyl group with an amino group of the protein; or Z=NH—CH$_2$ in the case of the reaction of a chloromethyl ketone with an amino group of the protein.

The protein $P_2$ substituted by the maleimide group or groups is obtained from the protein $P_2$ itself, or the correctly protected protein $P_2$, by substitution of suitable groups of the protein with the aid of a reagent which itself carries the maleimide group. Among these suitable groups, the following will be singled out in particular:

the phenol groups of the tyrosyl radicals contained in the protein. In this case, the reagent carrying the maleimide radical can be a reagent of the general formula Ib:

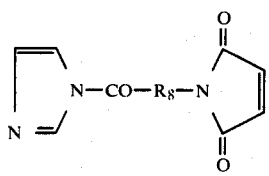

Ib i.e. an imidazolide according to the invention, which reacts with the phenol groups of the protein according to the equation:

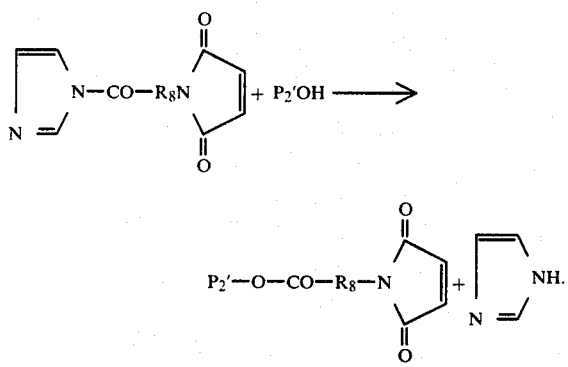

The reaction of the maleimide-carrying reagents with the protein $P_2$ is carried out in a homogeneous liquid phase, most commonly in water or a buffer solution. If necessitated by the solubility of the reactants, it is possible to add, to the reaction medium, a water-miscible organic solvent at a final concentration which can reach 20% by volume in the case of a tertiary alcohol, such as tertiary butanol, or 10% by volume in the case of dimethylformamide or tetrahydrofuran.

The reaction is carried out at ambient temperature for a time varying from a few minutes to a few hours, after which the low molecular weight products, and in particular the excess reactants, can be removed by dialysis or gel filtration. This process usually makes it possible to introduce between 1 and 15 substituent groups per mol of protein.

When using such compounds, the coupling with the protein $P_1$ is carried out by bringing the two proteins together in an aqueous solution having a pH of between 6 and 8, at a temperature not exceeding 30° C., for a time varying from 1 hour to 24 hours. The solution obtained is dialyzed, if appropriate, to remove the low molecular weight products, and the conjugate can then be purified by a variety of known methods.

Thus, the imidazolides according to the present invention are suitable coupling agents of proteins $P_1$ and $P_2$. They allow the obtention of new compounds having the statistical formula:

$$P_2''-O-CO-E-G \qquad IX$$

in which:
$P_2''$ represents the radical of a protein chosen from:
(a) any antibody or antibody fragment, any immunoglobulin or immunoglobulin fragment or any molecule derived from these molecules by artificial modification of any one of their functional groups; and
(b) the sub-unit A of ricin or any molecule derived from the said sub-unit A by artificial modification of any one of their functional groups,
one or more phenolic hydroxyl groups of the tyrosines having been removed from the said radical;
the oxygen atom is that belonging to the phenolic hydroxyl groups missing from the radical $P_2''$; and
E and G are as defined above.

Particular preference is given to the compounds of the formula IX in which E represents a group $-(CH_2)_p-$, in which p is an integer from 2 to 7, or a group:

$$-\underset{\underset{CH_2COOH}{|}}{CH}-$$

and G is a group of the structure $-S-S-X$, in which X is an activating radical chosen from the pyridin-2-yl and pyridin-4-yl groups which are unsubstituted or substituted by one or more halogens or alkyl, carboxyl or alkoxycarbonyl radicals, the phenyl group which is unsubstituted or substituted by one or more halogens or nitro, alkoxy, carboxyl or alkoxycarbonyl groups, or an alkoxycarbonyl group.

The products of the formula IX are prepared by reacting a product of the formula:

$$P_2''-OH$$

in which $P_2''$ is as defined above and the hydroxyl group is the phenolic hydroxyl missing from the tyrosines of the radical $P_2''$, with a compound of the above formula I. at a temperature of 10° to 40° C., in an aqueous solvent optionally containing a water-miscible organic solvent such as, for example, an ether solvent like dioxane or tetrahydrofuran.

The examples which follow provide a clearer understanding of the invention without limiting its scope.

In all these examples, the preparation of the conjugates will be described using the A chain of ricin in its native form, as obtained by the process described in U.S. Pat. No. 4,340,535.

The antibodies used in these examples are:
the monoclonal antibody T101 directed against the antigen T65 present on human T lymphocytes and numerous lines of human T leukemia cells. This antibody is the one described in Journal of Immunology 125(2), 725-7 (1980). It is commercially available from HYBRITECH Inc., San Diego, Calif., USA.
or the monoclonal antibody AT15E directed against the antigen Thy 1.2 of murine lymphocytes. This antibody is the one described in Journal of Immunology 122, 2491-8 (1979) and has been obtained from the hybridoma described in Hybridoma 1(1), 13-17 (1981).
or a monoclonal antibody anti-DNP.

I—EXAMPLE 1

$P_1$=antibody T101 into which an SH has been introduced via the amines.
$P_2$=A chain of ricin into which an activated disulfide group has been introduced via the hydroxyl of the tyrosines.

(A) Preparation of the coupling reagent

The coupling reagent is the imidazolide derived from 3-(pyridin-2-yldisulfanyl)propionic acid (PDPA). This imidazolide is obtained in a single step from PDPA and carbonyldiimidazole (CDI).

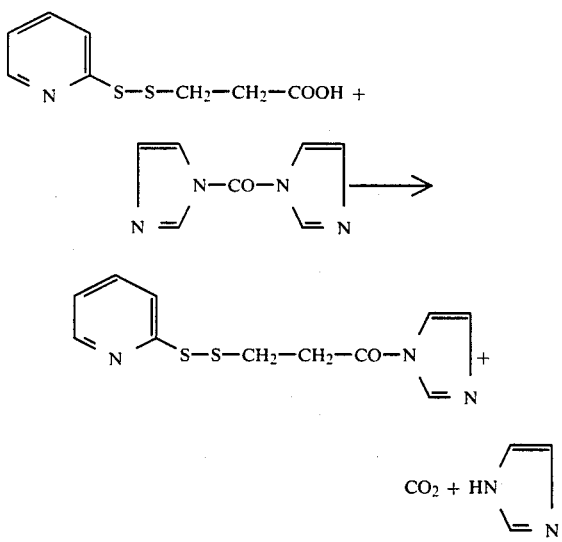

430 g of 3-(pyridin-2-yldisulfanyl)propionic acid are dissolved in 2 ml of THF. 405 mg of CDI are added to this solution. The mixture is stirred for ¼ h at 25° C. The evolution of CO₂ gas is observed. The reaction medium is used directly and immediately without purification.

(B) Preparation of the correctly functionalized A chain of ricin (1) Blocking of the natural thiol with N-ethylmaleimide 15 ml of an aqueous solution of the A chain of ricin containing 8 mg/ml (i.e. 4.1 micromol of A chain) are treated with an aqueous solution of 2-mercaptoethanol so that the final concentration of the latter is 1 percent. The solution is left to stand for one hour and then dialyzed continuously against 125 mM phosphate buffer of pH 7, which is renewed for 40 hours at a rate of 300 ml/hour. Using ELLMAN's method (Methods in Enzymology 25, 457, 1972), 0.9 equivalent of SH was determined per mol of A chain of ricin.

This SH group is blocked with N-ethylmaleimide by the method described in Methods in Enzymology 11, 541 (1967). To do this, the A chain of ricin obtained in the previous step is incubated for 2 hours at 30° C. in the presence of 20 equivalents of N-ethylmaleimide per mol of A chain. The excess reagent is removed by continuous dialysis against 125 mM phosphate buffer of pH 7, which is renewed for 20 hours at a rate of 500 ml/hour. This gives 13 ml of a solution of A chain of ricin containing 7 mg/ml and no longer possessing thiol groups which can be determined by ELLMAN's reagent. The product thus obtained is subsequently called A chain (NEM).

(2) Modification of the tyrosines 300 microliters of the previously obtained solution of coupling reagent in THF are added dropwise to 18 mg of A chain (NEM) in 10 ml of 125 mM phosphate buffer of pH 7 (i.e. 0.6 micromol). The reaction medium is stirred for 15 minutes at 25° C. and the solution is then purified to remove the excess reagent by dialysis against 125 mM phosphate buffer of pH 7. This gives 9.5 ml of a solution of modified A chain (NEM) containing 1.55 mg/ml of protein.

By spectrophotometric analysis at 343 nm of the pyridine-2-thione released by exchange with 2-mercaptoethanol, it is found that the modified A chain (NEM) obtained carries 1.6 activating groups per mol of A chain (NEM).

(C) Preparation of the modified antibody 25 microliters of a solution of S-acetylmercaptosuccinic anhydride (SAMSA) containing 170 mg/ml in dimethylformamide are added to 45 mg of a solution of antibody T101 containing 9 mg/ml, i.e. 0.3 micromol. The reaction medium is stirred for 2 hours at 4° C. and then purified to remove the reagents by dialysis against 125 mM phosphate buffer of pH 7 for 24 hours at a rate of 400 ml/hour. This gives 4.1 ml of a solution of modified antibody containing 8.6 mg/ml. 0.46 ml of a 0.5M solution of hydroxylamine hydrochloride is added to this antibody solution. After incubation for 1 h at 30° C., the reaction medium is purified to remove the reagents by dialysis against 125 mM phosphate buffer of pH 7.

By spectrophotometric analysis of the SH groups thus freed by ELLMAN's method, it is found that the antibody obtained carries 5 activating groups per mol of antibody.

(D) Preparation of the immunotoxin 5.2 ml of the solution of modified A chain (0.27 micromol) are added to 2.1 ml of the solution of antibody obtained above (i.e. 0.11 micromol). The mixture is incubated for 5 hours at 30° C.

The reaction medium is purified on a Sephadex G100 column in the manner indicated in Example 1. This gives 17 ml of an immunotoxin solution containing 1.1 mg/ml (i.e. 18.7 mg). This solution contains 0.32 mg/ml of modified A chain (NEM). The average degree of coupling of this preparation is 2 A chains (NEM) per mol of antibody.

This gives an immunotoxin of the formula V above in which:

A' is the radical of the sub-unit A of ricin in which the SH groups are blocked with N-ethylmaleimide;
P' is the radical of the antibody T101; and
W' is a group of the formula:

$$-(NH-Y'-E')_n-S-S-E-Y-Z-$$

in which:
Y' is —CO—
E' is $-CH_2CH_2-$
E is $$\begin{array}{l}-CH-\\ \quad |\\ CH_2COOH\end{array}$$

Y is —CO—
Z is —O—
n is 1.

(E) Immunotoxin activity test

The fundamental biological property of the A chain of ricin is to inhibit protein synthesis in eucaryotic cells by degradation of the ribosomal subunit 60S.

The tests performed are therefore tests for the inhibition of protein synthesis: either on an acellular model (test no. 1) or on a cell model (test no. 2).

(1) The acellular model (test no. 1)

The in vitro protocol uses appropriately complemented, subcellular fractions of rat liver capable of incorporating $^{14}C$-phenylalanine in the presence of an artificial messenger RNA: polyuridylic acid.

The procedure employed for preparing the subcellular fractions and measuring the incorporation of $^{14}C$-phenylalanine is an adaptation of the method described in Biochemica Biophysica Acta 312, 608–615 (1973), using both a microsomal fraction and a cytosol fraction of the rat hepatocytes. The sample containing the A chain is introduced in the form of a solution appropriately diluted in a 50 mM Tris HCl buffer of pH 7.6, containing 0.2% of 2-mercaptoethanol and 15 micrograms/ml of bovine serum albumin. The count data are used to calculate, relative to a control medium without inhibitor, the percentage inhibition of the incorporation of $^{14}C$-phenylalanine into the proteins for each reaction medium containing A chain of ricin. These values together make it possible to determine the concentration of A chain of ricin (or $IC_{50}$) which inhibits the incorporation of the $^{14}C$-phenylalanine by 50% under the experimental conditions.

(2) The cell model (test no. 2)

This test measures the effect of the substances studied on the incorporation of $^{14}C$-leucine into cancerous cells in culture.

The cells used depend on the specificity of the antibody chosen to manufacture the immunotoxin. In this example, they are cells of the CEM human lymphoblastoid line which naturally carry the antigen T65.

These cells are incubated in the presence of preparations of the substances to be studied, and then, when incubation has ended, they are subjected to measurement of their degree of incorporation of $^{14}C$-leucine. This measurement is carried out by a technique adapted from the one described in Journal of Biological Chemistry 249(11), 3557–3562 (1974), using the tracer $^{14}C$-leucine to determine the degree of protein synthesis. The radioactivity incorporated is determined here on the whole cells isolated by filtration.

On the basis of these determinations, it is possible to draw the dose/effect curves, plotting, on the abscissa, the concentration of the substances studied, and, on the ordinate, the incorporation of $^{14}C$-leucine expressed as a percentage of the incorporation by control cells in the absence of the substance to be studied.

It is thus possible to determine, for each substance studied, the concentration which causes a 50 percent inhibition of the incorporation of $^{14}C$-leucine into the cells, or "50% inhibitory concentration" ($IC_{50}$). A check was carried out to show that the measurement of the incorporation of the $^{14}C$-leucine into the whole cells resulted in the determination of $IC_{50}$ values identical to those obtained by the conventional method for the measurement of protein synthesis.

(3) Results (a) Test no. 1 (acellular model)

The inhibitory activity of the modified A chain (NEM) was determined. The $IC_{50}$ is equal to $3.6 \cdot 10^{-10}$ mol/liter. The $IC_{50}$ of the control A chain is $1.2 \cdot 10^{-10}$ mol/l in the experiment. There is therefore no significant loss of activity of the modified A chain.

(b) Test no. 2 (cell model)

Under experimental conditions identical to those of Example 2, the $IC_{50}$ in the presence of activator (50 nM monensin) is $1.2 \cdot 10^{-12}$ mol/l, which represents an activity $5 \cdot 10^4$ times greater than that of the A chain ($IC_{50} = 6 \cdot 10^{-8}$ mol/l).

II—EXAMPLE 2

$P_1$ = antibody T101 into which an SH group has been introduced via the amines.

$P_2$ = A chain of ricin into which a maleimide group has been introduced via the hydroxyl of the tyrosines.

(A) Preparation of the coupling agent

The coupling agent is the imidazolide derived from maleimidocaproic acid. This imidazolide is obtained in a single step from maleimidocaproic acid and carbonyldiimidazole (CDI):

$$\text{maleimide-N-(CH}_2)_5\text{-COOH} +$$

$$\text{imidazole-N-CO-N-imidazole} \longrightarrow$$

$$\text{maleimide-N-(CH}_2)_5\text{-CO-N-imidazole} +$$

$$CO_2 + HN\text{-imidazole}$$

422 mg of maleimidocaproic acid are dissolved in 2 ml of THF. 405 mg of CDI are added to this solution. The mixture is stirred for ¼ h at ambient temperature. The evolution of $CO_2$ gas is observed. The reaction medium is used directly without purification.

(B) Preparation of the correctly functionalized A chain of ricin (1) Blocking with N-ethylmaleimide:

Identical to that described in Example 1.

(2) Modification of the tyrosines 300 microliters of the previously obtained solution of coupling reagent in THF are added dropwise to 18 mg of A chain (NEM) in 10 ml of 125 mM phosphate buffer of pH 7 (i.e. 0.6 micromol). The reaction medium is stirred for 15 minutes at 25° C. and the solution is then purified to remove the excess reagent by dialysis against 125 mM phosphate buffer of pH 7. This gives 20 ml of a solution of modified A chain (NEM) containing 1.45 mg/ml. By determination of the maleimide groups with the aid of $^{14}C$-cysteine, it is found that the A chain obtained carries an average of 1 activating group per mol of A chain (NEM).

(C) Preparation of the modified antibody

Identical to that described in Example 1.

(D) Preparation of the immunotoxin 5.8 ml of the solution of modified A chain (0.28 micromol) are added to 2.1 ml of the antibody solution obtained above (i.e. 0.11 micromol).

THe mixture is incubated for 1 h at 30° C. The residual maleimide groups are blocked with 5 micromol of cysteine. Incubation takes 1 hour at 30° C. The reaction mixture is purified on Sephadex C100 by the method described above. This gives 19.5 ml of an immunotoxin solution containing 1.05 mg/ml (i.e. 20.5 mg). This solution contains 0.31 mg/ml of modified A chain (NEM). The average degree of coupling of this preparation is 2 A chains (NEM) per mol of antibody.

This gives an immunotoxin of the formula V above in which:

A' is the radical of the sub-unit A of ricin in which the SH groups are blocked with N-ethylmaleimide;
P' is the radical of the antibody T101; and
W' is a group of the formula:

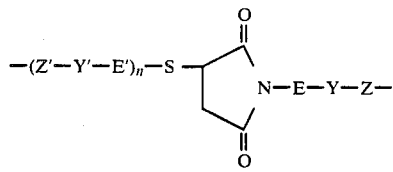

in which:
Z' is —NH—
Y' is —CO—
E' is

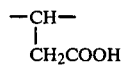

E is —CH$_2$—CH$_2$—
Y is —CO—
Z is —O—
n is 1.

(E) Activity tests (a) Test no. 1 (acellular model)

The inhibitory activity of the modified A chain was determined. The IC$_{50}$ is equal to $10 \cdot 10^{-10}$ mol/l. The IC$_{50}$ of the control A chain is $1.1 \cdot 10^{-10}$ mol/l in the experiment. Despite a considerable loss of activity, the modified A chain still retains a high capacity to inhibit protein synthesis.

(b) Test no. 2 (cell model)

Under experimental conditions identical to those of Example 1, the IC$_{50}$ in the presence of activator (50 nM monensin) is $3 \cdot 10^{-11}$ mol/l, which represents an activity $3 \cdot 10^3$ times greater than that of the A chain (IC$_{50}$=$6 \cdot 10^{-8}$ mol/l).

III—EXAMPLE 3

P$_1$=A chain of ricin in the native state.
P$_2$=antibody T101 into which an activated disulfide group has been introduced via the hydroxyl of the tyrosines.

(A) Preparation of the coupling reagent

Identical to that described in Example 1.

(B) Preparation of the modified antibody 34 microliters of the previously described THF solution diluted to ½ (200 equivalents/mol of IgG) are added dropwise to 12.8 mg of antibody T101 in 2.8 ml of 125 mM phosphate buffer of pH 7. The reaction medium is stirred for ¼ h at ambient temperature and then purified by dialysis to give 2.6 ml of a solution of modified antibody containing 4.55 mg/ml.

By spectrophotometric analysis at 343 nm of the pyridine-2-thione released by exchange with 2-mercaptoethanol, it is found that the antibody obtained carries 2.2 activating groups per mol of antibody.

(C) Preparation of the immunotoxin 2.5 ml of a solution of activated antibody containing 4.55 mg/ml (i.e. 0.075 micromol of antibody) are added to 750 microliters of a solution of A chain of ricin containing 7.1 mg/ml (i.e. 0.177 micromol). The mixture is incubated for 18 h at 25° C. The reaction medium is purified on a Sephadex G100 column in the manner described in Example 1. This gives 13 ml of an immunotoxin solution containing 0.8 mg/ml (i.e. 10.4 mg). This solution contains 0.2 mg/ml of A chain. The average degree of coupling of this preparation is 1.5 A chains per mol of antibody.

This gives an immunotoxin of the formula VI above in which:

A' is the radical of the sub-unit A of ricin;
P' is the radical of the antibody T101;
W' is a group of the formula:

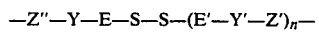

in which:
Z" is —O—
Y is —CO—
E is —CH$_2$—CH$_2$—
n is zero; and
m is 1.5.

(D) Activity tests

Test no. 2 (cell model)

Under experimental conditions identical to those of Example 1, the IC$_{50}$ in the presence of activator (50 nM monensin) is $3.5 \cdot 10^{-13}$ mol/l, which represents a cytotoxic activity $1.5 \cdot 10^5$ times greater than that of the A chain in the same experiment (IC$_{50}$=$0.6 \cdot 10^{-8}$ mol/l).

IV—EXAMPLE 4

P$_1$=A chain of ricin in the native state.
P$_2$=antibody T101 into which a maleimide group has been introduced via the hydroxyl of the tyrosines.

(A) Preparation of the coupling reagent

Identical to that of Example 2.

(B) Preparation of the modified antibody 34 microliters of the previously described THF solution diluted to ½ (200 equivalents/mol of IgG) are added dropwise to 12.8 mg of antibody T101 in 2.8 ml of 125 mM phosphate buffer of pH 7. The reaction medium is stirred for ¼ hour at ambient temperature and then purified by dialysis to give 2.6 ml of a solution of modified antibody containing 4.5 mg/ml.

By determination of the maleimide groups with the aid of $^{14}$C-cysteine, it is found that the antibody obtained carries 4.0 activating groups per mol of antibody.

(C) Preparation of the immunotoxin 2.5 ml of a solution of activated antibody containing 4.5 mg/ml (i.e. 0.075 micromol of IgG) are added to 850 microliters of a solution of A chain of ricin containing 7.1 mg/ml (i.e. 0.20 micromol). The mixture is incubated for 1 h at 25° C. The residual maleimide groups are blocked with 6 micromol of cysteine. Incubation takes 1 h at 30° C. The reaction medium is purified on a Sephadex G100 column in the manner described in Example 1 to give 11 ml of an immunotoxin solution containing 0.76 mg/ml (i.e. 8.36 mg). This solution contains 0.29 mg/ml of A chain. The average degree of coupling of this preparation is 3 A chains per mol of antibody.

This gives an immunotoxin of the formula VI above in which:
A' is the radical of the sub-unit A of ricin;
P' is the radical of the antibody T101;
W' is a group of the formula:

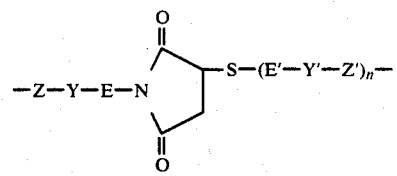

in which:
Z is —O—
Y is —CO—
E is —(CH$_2$)$_5$—
n is zero; and
m is 3.

(D) Activity tests

Test no. 2 (cell model)

Under experimental conditions identical to those of Example 1, the IC$_{50}$ of the immunotoxin in the presence of activator (50 nM monensin) is $1.7 \cdot 10^{-12}$ mol/l, which represents an activity $3 \cdot 10^3$ times greater than that of the A chain in the same experiment.

What is claimed is:

1. A compound having a formula:

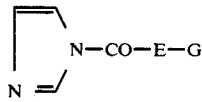

in which E represents a group —(CH$_2$)$_p$—, in which p is an integer from 2 to 7, or a group:

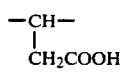

and G is a group of the structure —S—S—X, in which X is an activating radical which is a pyridin-2-yl or pyridin-4-yl group which is unsubstituted by one or more halogens or C$_{1-5}$ alkyl, carboxyl or C$_{1-5}$ alkoxycarbonyl groups; a phenyl group which is unsubstituted or substituted by one or more halogens or nitro, C$_{1-5}$ alkoxy, carboxyl or C$_{1-5}$ alkoxycarbonyl groups; or an C$_{1-5}$ alkoxycarbonyl group.

2. The compounds of claim 1 wherein X is pyridine-2-yl or pyridine-4-yl and E is —CH$_2$—CH$_2$.

* * * * *

UNITED STATES PATENT AND TRADEMARK OFFICE
CERTIFICATE OF CORRECTION

PATENT NO. : 4,670,563
DATED : June 2, 1987
INVENTOR(S) : Franz JANSEN and Pierre GROS It is certified that error appears in the above-identified patent and that said Letters Patent is hereby corrected as shown below:

Column 22, line 28, after "unsubstituted" insert --or substituted--.

Signed and Sealed this

Seventh Day of January, 1992

*Attest:*

HARRY F. MANBECK, JR.

*Attesting Officer*  *Commissioner of Patents and Trademarks*